US012629014B2

(12) United States Patent
Tatur et al.

(10) Patent No.: US 12,629,014 B2
(45) Date of Patent: May 19, 2026

(54) DEVICE AND METHOD FOR AUTOMATICALLY EVALUATING VISUAL EQUIPMENT

(71) Applicant: Essilor International, Charenton-le-Pont (FR)

(72) Inventors: Guillaume Tatur, Charenton-le-Pont (FR); Laurent Calixte, Charenton-le-Pont (FR); Sébastien Fricker, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 312 days.

(21) Appl. No.: 18/546,158

(22) PCT Filed: Jan. 13, 2022

(86) PCT No.: PCT/EP2022/050615
§ 371 (c)(1),
(2) Date: Aug. 11, 2023

(87) PCT Pub. No.: WO2022/171377
PCT Pub. Date: Aug. 18, 2022

(65) Prior Publication Data
US 2024/0115126 A1 Apr. 11, 2024

(30) Foreign Application Priority Data

Feb. 12, 2021 (EP) ..................................... 21305190

(51) Int. Cl.
*A61B 3/00* (2006.01)
*G16H 50/50* (2018.01)
(52) U.S. Cl.
CPC ........... *A61B 3/0025* (2013.01); *G16H 50/50* (2018.01)

(58) Field of Classification Search
CPC .... A61B 3/00; A61B 3/10; A61B 3/12; A61B 3/02; A61B 3/3102; A61B 3/1025;
(Continued)

(56) References Cited

U.S. PATENT DOCUMENTS

| | | |
|---|---|---|
| 2012/0019776 A1 | 1/2012 | Giraudet |
| 2013/0335405 A1 | 12/2013 | Scavezze et al. |
| (Continued) | | |

FOREIGN PATENT DOCUMENTS

| | | |
|---|---|---|
| JP | 2005-513526 A | 5/2005 |
| WO | WO 2020/193370 A1 | 10/2020 |
| WO | WO 2020/193436 A | 10/2020 |

OTHER PUBLICATIONS

Combined Chinese Office Action and Search Report issued on Jun. 11, 2025, in Chinese Patent Application No. 202280010094.3 (with English Translation), 16 pages.
(Continued)

*Primary Examiner* — Jie Lei
(74) *Attorney, Agent, or Firm* — Oblon, McClelland, Maier & Neustadt, L.L.P.

(57) ABSTRACT

A device for evaluating visual equipment models corresponding to real visual equipments. The device includes at least one input adapted to obtain parameters including a prescription for a given human wearer of any one of the real visual equipments, a set of ophthalmic lenses pre-selected on the basis of those parameters, at least one processor configured, for each pre-selected ophthalmic lens, to obtain a visual equipment model including a virtual ophthalmic lens defined by the same characteristics as the pre-selected ophthalmic lens, obtain a wearer model from the parameters, the visual equipment model cooperating with the wearer model, obtain an environment and visual task model including a sequence of points to be looked at by the wearer model,
(Continued)

Obtain plurality of parameters — 30

Pre-select lens set — 32

Obtain Me, Mw, Mt — 34

Evaluate performance of Me worn by Mw and combined with Mt — 36 and evaluate a performance of the visual equipment model worn by the wearer model and combined with the environment and visual task model.

15 Claims, 2 Drawing Sheets

(58) Field of Classification Search
CPC ... A61B 3/1225; A61B 3/0016; A61B 3/0025; A61B 3/0041; A61B 3/0075; A61B 3/0091; A61B 3/0083; A61B 3/15; A61B 3/152; A61B 3/113; A61B 3/117; G02C 7/02; G02C 7/028; G02C 7/027; G02C 7/024; G02C 7/10; G02C 13/00; G02C 13/003; G02C 13/005; G02C 13/001; G16H 50/50
USPC .......... 351/227, 204, 159.75, 223, 221, 206, 351/208, 210, 211, 246
See application file for complete search history.

(56) References Cited

U.S. PATENT DOCUMENTS

| | | |
|---|---|---|
| 2015/0049304 A1 | 2/2015 | Cussac |
| 2015/0055085 A1 | 2/2015 | Fonte et al. |
| 2015/0055086 A1 | 2/2015 | Fonte et al. |
| 2015/0154322 A1 | 6/2015 | Fonte et al. |
| 2015/0154678 A1 | 6/2015 | Fonte et al. |
| 2015/0154679 A1 | 6/2015 | Fonte et al. |
| 2015/0212343 A1 | 7/2015 | Fonte et al. |
| 2016/0062151 A1 | 3/2016 | Fonte et al. |
| 2016/0062152 A1 | 3/2016 | Fonte et al. |
| 2016/0246078 A1 | 8/2016 | Choukroun et al. |
| 2017/0068121 A1 | 3/2017 | Fonte et al. |
| 2017/0269385 A1 | 9/2017 | Fonte et al. |
| 2018/0299704 A1 | 10/2018 | Fonte et al. |
| 2019/0113770 A1 | 4/2019 | Tranvouez-Bernardin et al. |
| 2019/0146246 A1 | 5/2019 | Fonte et al. |
| 2019/0246095 A1 | 8/2019 | Kishimoto |
| 2020/0285081 A1 | 9/2020 | Fonte et al. |

OTHER PUBLICATIONS

International Search Report & Written Opinion issued Apr. 14, 2022 in PCT/EP2022/050615, filed on Jan. 13, 2022, 13 pages.
Japanese Office Action issued Aug. 26, 2025, in corresponding Japanese Patent Application No. 2023-544382 (with English Translation), 11 pages.

DEVICE AND METHOD FOR AUTOMATICALLY EVALUATING VISUAL EQUIPMENT

FIELD OF THE DISCLOSURE

The present disclosure relates to a device and method for automatically evaluating visual equipment.

More particularly, the disclosure relates to a device and method for automatically evaluating a plurality of visual equipment models respectively corresponding to a plurality of real visual equipments for a given human wearer of any one of those real visual equipments to carry out one or more real visual tasks in one or more real environments.

BACKGROUND OF THE DISCLOSURE

Today, in an optician's store, in order to determine the best piece of visual equipment for a customer, ECPs (Eye Care Professionals) usually rely on their technical knowledge about optical designs, coatings and frames.

Customers can try on frames.

In this respect, eyeglasses simulation methods are known, in which the customer can try and subjectively evaluate equipment in a virtual environment through a virtual reality device. Such an eyeglasses wearing simulation method and device is disclosed by document EP-A-2 749 207.

Thus, customers can experience and choose a piece of visual equipment among a list of pieces of visual equipment after virtually testing them. Rendering simulation usually encompasses lens design and added values, e.g. coating, spectral filtering and/or dimmer control. In addition, a user interface may drive customers through the decision process.

However, selecting the most appropriate piece of visual equipment, including frame, lens and added values, requires knowing technical details about the product and how they will impact visual equipment wearer performance for the specific wearer considered. This is a difficult task both for the ECP and for the customer.

In addition, it is also difficult for the ECP to explain to a customer the benefits of a chosen design and/or added value, because the customer generally lacks technical knowledge about lens designs or coatings.

Therefore, there is a need for a tool making it possible to easily and promptly determine the most appropriate item of visual equipment for a given customer and making it possible for the customer to know in a quick and simple manner the benefits of that equipment item, either in a physical store, or online, e.g. through a visual equipment selling Web site or application.

Document WO 2020/193436 A1 discloses a device and method for evaluating a performance of a piece of visual equipment intended for a human wearer to carry out a visual task. The described device and method involve a virtual "avatar" that is a virtual model of the human wearer, in addition to virtual models of the visual task and of the scene where the virtual, simulated visual task is to be carried out. This makes it possible to apply the performance evaluation to a given wearer population i.e. groups of wearers considered to have similar characteristics.

However, although such evaluation is made in a potentially efficient and economic manner for groups of wearers thanks to the "avatar", it does not take account of the very specific habits of each individual wearer, including motion, task, environment, in addition to eye-related parameters.

Namely, a given individual, although having comparable characteristics to other individuals of a defined group of wearers, may nevertheless wear and use the piece of visual equipment differently from other individuals in the same group of wearers. For example, a given individual may wish to use the piece of visual equipment for other visual tasks than the one for which the performance has been evaluated and those other visual tasks will not necessarily be the same as for the other individuals of the same group of wearers. In addition, the other visual tasks will possibly be carried out in environments differing from the one for which the performance has been evaluated, with different distances to objects of the scene, different lighting, far vision instead of near vision, etc.

Furthermore, instead of having a single choice i.e. the piece of visual equipment for which the evaluated performance is considered to be the "best", each individual may wish to select his/her preferred piece of visual equipment depending on his/her own personal criteria, among a pre-selection of various propositions and recommendations made by the ECP, either in a shop, or online.

Thus, there is a need for further customizing the piece of visual equipment to each given individual, in order to provide for each individual, rather than a "ready-to-wear" piece of visual equipment, the possibility of wearing "made-to-measure" visual equipment, taking account of both the individual per se and the individual's visual task habits and intended uses of such visual equipment, thanks to an overall personalized evaluation of the visual equipment performance for that individual.

SUMMARY OF THE DISCLOSURE

An object of the disclosure is to overcome the above-mentioned drawbacks of the prior art.

To that end, the disclosure provides a device for evaluating a plurality of visual equipment models respectively corresponding to a plurality of real visual equipments for a given human wearer of any one of those real visual equipments to carry out at least one real visual task in at least one real environment, each one of the real visual equipments comprising at least one ophthalmic lens, wherein the device comprises:

at least one input adapted to:

obtain a plurality of parameters comprising at least a prescription for at least one eye of the given human wearer;

a set of ophthalmic lenses pre-selected on the basis of that plurality of parameters;

at least one processor configured, for each one of the pre-selected ophthalmic lenses, to:

obtain a visual equipment model, which is a virtual model of a given one of the real visual equipments, the visual equipment model comprising at least one virtual ophthalmic lens defined by the same characteristics as the above-mentioned one of the pre-selected ophthalmic lenses;

obtain a wearer model, which is a virtual model of the given human wearer, the wearer model being built from at least one parameter of the plurality of parameters, the visual equipment model cooperating with the wearer model;

obtain an environment and visual task model, which is a virtual model of the at least one real environment and the at least one real visual task, the environment and visual task model comprising at least a sequence of points to be looked at by the wearer model;

evaluate a performance of the visual equipment model worn by the wearer model and combined with the environment and visual task model.

Therefore, by using data that are all customized for the specific human wearer considered and starting from existing real or virtual pieces of visual equipment that are also pre-selected as a function of the specific human wearer considered, avatar simulations make it possible to evaluate in an automated manner the performance of each piece of equipment for that specific wearer.

Besides, the evaluation results can be used for demonstrating to the customer the benefits of a chosen visual equipment design.

In addition, the avatar is used not only for simulating the activity of the wearer, or any eye-related parameter such as the prescription, the eye gaze direction or the head posture, but also for simulating the wearer's motion behavior in a customized activity and in a customized environment.

Thus, a better visual equipment recommendation, most relevant according to the human wearer's motion behavior, can be achieved.

The above-mentioned plurality of parameters may further comprise at least one parameter related to vision of the given human wearer.

The above-mentioned plurality of parameters may further comprise at least one parameter related to a manner in which the given human wearer intends to use the above-mentioned one of the real visual equipments.

The above-mentioned plurality of parameters may further comprise at least one parameter related to the given human wearer's lifestyle, the lifestyle being related to at least one type of activity in the course of which the given human wearer intends to use the above-mentioned one of the real visual equipments.

The at least one parameter related to the given human wearer's lifestyle may be used for weighting the above-mentioned performance and/or for modifying the above-mentioned environment and visual task model.

In an embodiment, the environment and visual task model comprises models of objects acquired by tridimensional scanning of real objects of the real environment.

In another embodiment, the environment and visual task model comprises models of objects defined via a software interface.

In that embodiment, the objects may be taken among predefined objects, dimensions and/or positions of which are adjusted to match real objects of the real environment.

The wearer model may comprise a movable head model, which is a virtual model of a head of said given human wearer.

The head model may comprise at least one virtual eye, which is a virtual model of at least one eye of the given human wearer, the at least one virtual eye being rotationally movable with respect to the head model.

The above-mentioned plurality of parameters may further comprise data related to motion of the at least one eye of the given human wearer, in contribution to visual behavior and/or to motion of the head of the given human wearer, in contribution to visual behavior.

The wearer model may further comprise a virtual torso of the wearer, which is a virtual model of a torso of the given human wearer.

The virtual torso may be movable in the environment and visual task model.

The head model may be rotationally movable with respect to the virtual torso.

The above-mentioned plurality of parameters may further comprise data related to motion of the torso of the given human wearer, in contribution to visual behavior.

The real visual equipments may further comprise an eyeglasses frame and the above-mentioned plurality of parameters may further comprise data related to the frame.

The at least one processor may be further configured to represent graphically the wearer model carrying out a virtual model of the at least one real visual task in the environment and visual task model.

To the same end as mentioned above, the disclosure also provides a computer-implemented method for evaluating a plurality of visual equipment models respectively corresponding to a plurality of real visual equipments for a given human wearer of any one of those real visual equipments to carry out at least one real visual task in at least one real environment, each one of the real visual equipments comprising at least one ophthalmic lens, wherein the method comprises:

obtaining a plurality of parameters comprising at least a prescription for at least one eye of the given human wearer;

pre-selecting a set of ophthalmic lenses on the basis of that plurality of parameters;

running the following steps by at least one processor for each one of the pre-selected ophthalmic lenses:

obtain a visual equipment model, which is a virtual model of a given one of the real visual equipments, the visual equipment model comprising at least one virtual ophthalmic lens defined by the same characteristics as the above-mentioned one of the pre-selected ophthalmic lenses;

obtain a wearer model, which is a virtual model of the given human wearer, the wearer model being built from at least one parameter of the above-mentioned plurality of parameters, the visual equipment model cooperating with the wearer model;

obtain an environment and visual task model, which is a virtual model of the at least one real environment and the at least one real visual task, the environment and visual task model comprising at least a sequence of points to be looked at by the wearer model;

evaluate a performance of the visual equipment model worn by the wearer model and combined with the environment and visual task model.

In particular embodiments, the method succinctly described above is executed by the device succinctly described above according to the disclosure, in any of its embodiments.

To the same end as mentioned above, the disclosure further provides a computer program product for evaluating a plurality of visual equipment models respectively corresponding to a plurality of real visual equipments for a given human wearer of any one of those real visual equipments to carry out at least one real visual task in at least one real environment, each one of the real visual equipments comprising at least one ophthalmic lens, wherein the computer program product comprises one or more sequences of instructions that are accessible to a processor and that, when executed by the processor, cause the processor to:

obtain a plurality of parameters comprising at least a prescription for at least one eye of the given human wearer;

pre-select a set of ophthalmic lenses on the basis of that plurality of parameters;

run the following steps by at least one processor for each one of the pre-selected ophthalmic lenses:

obtain a visual equipment model, which is a virtual model of a given one of the real visual equipments, the visual equipment model comprising at least one virtual ophthalmic lens defined by the same characteristics as the above-mentioned one of the preselected ophthalmic lenses;

obtain a wearer model, which is a virtual model of the given human wearer, the wearer model being built from at least one parameter of the plurality of parameters, the visual equipment model cooperating with the wearer model;

obtain an environment and visual task model, which is a virtual model of the at least one real environment and the at least one real visual task, the environment and visual task model comprising at least a sequence of points to be looked at by the wearer model;

evaluate a performance of the visual equipment model worn by the wearer model and combined with the environment and visual task model.

To the same end as mentioned above, the disclosure further provides a non-transitory computer-readable storage medium, wherein it stores one or more sequences of instructions that are accessible to a processor and that, when executed by the processor, cause the processor to:

obtain a plurality of parameters comprising at least a prescription for at least one eye of the given human wearer;

pre-select a set of ophthalmic lenses on the basis of that plurality of parameters;

run the following steps by at least one processor for each one of the pre-selected ophthalmic lenses:

obtain a visual equipment model, which is a virtual model of a given one of the real visual equipments, the visual equipment model comprising at least one virtual ophthalmic lens defined by the same characteristics as the above-mentioned one of the preselected ophthalmic lenses;

obtain a wearer model, which is a virtual model of the given human wearer, the wearer model being built from at least one parameter of the plurality of parameters, the visual equipment model cooperating with the wearer model;

obtain an environment and visual task model, which is a virtual model of the at least one real environment and the at least one real visual task, the environment and visual task model comprising at least a sequence of points to be looked at by the wearer model;

evaluate a performance of the visual equipment model worn by the wearer model and combined with the environment and visual task model.

As the advantages of the method, of the computer program product and of the computer-readable storage medium are similar to those of the device, they are not repeated here.

The computer program product and the computer-readable storage medium are advantageously configured for executing the method in any of its execution modes.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DETAILED DESCRIPTION OF EMBODIMENTS

Figure 1:
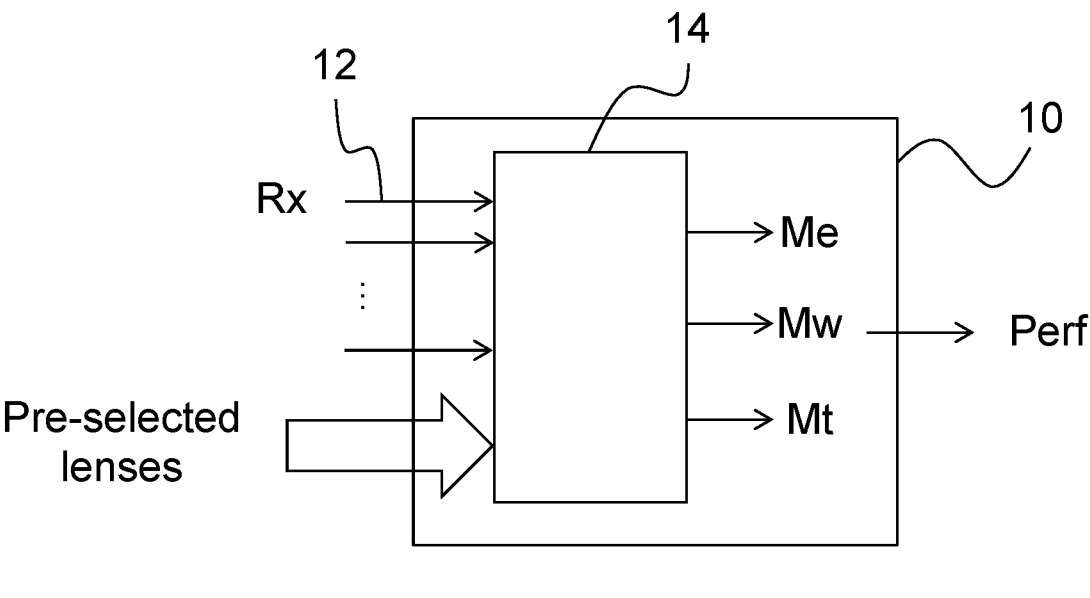
FIG. 1 is a schematic view of a device according to the disclosure, in a particular embodiment.

In the description which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may embodied in a wide variety of contexts. Embodiments discussed herein are merely representative and do not limit the scope of the disclosure. It will also be obvious to one skilled in the art that all the technical features that are defined relative to a process can be transposed, individually or in combination, to a device and conversely, all the technical features relative to a device can be transposed, individually or in combination, to a process.

The terms "comprise" (and any grammatical variation thereof, such as "comprises" and "comprising"), "have" (and any grammatical variation thereof, such as "has" and "having"), "contain" (and any grammatical variation thereof, such as "contains" and "containing"), and "include" (and any grammatical variation thereof such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises", "has", "contains", or "includes" one or more steps or elements possesses those one or more steps or elements, but is not limited to possessing only those one or more steps or elements.

FIG. 1 shows a particular embodiment of a device 10 for evaluating one or more visual equipment models respectively corresponding to one or more real "visual equipments" i.e. pieces or items of visual equipment for a given human wearer.

A human wearer is a human being wearing any one of those real visual equipments for carrying out at least one real visual task in at least one real environment.

Each one of the real visual equipments comprises at least one ophthalmic lens and may be an ophthalmic lens or pair of ophthalmic lenses, or a solar lens or pair of solar lenses, or an ophthalmic solar lens or pair of ophthalmic solar lenses. It may be in the form of eyeglasses or contact lenses.

The device 10 comprises one or more inputs 12.

The one or more inputs 12 are adapted to obtain one or more parameters.

As shown in FIG. 1, the parameters comprise at least a prescription Rx, for at least one eye of the given human wearer. The prescription Rx may include sphere and/or cylinder and/or axis and/or addition and/or prism.

Optionally, the at least one input 12 may be adapted to also obtain one or more of the following parameters, which are briefly listed below and detailed hereinafter:

parameters related to vision of the given human wearer, regarding for instance physiology and/or visual behavior;

data related to the frame, if any one of the real visual equipments comprises an eyeglasses frame;

parameters regarding the lifestyle of the wearer;
parameters regarding the environment.

The parameters related to vision may include, in addition to the prescription:

age,
gender,
half-pupillary-distances,
height and main other dimensions of body,
head and body axes and rotation centers,
Harmon's distance, or reading distance,
maximum visual acuity,
visual acuity sensitivity to aberrations,
objective/subjective accommodation reserve,
range of motion of the head,
range of motion of the eyes,
kyphosis,
phorias,
fusional reserves (maximal amount of eyes convergence or divergence while maintaining binocular single vision),
sensory dominant eye,
head-eye coefficient,
gaze dominant eye,
near vision behavior,
hand laterality,
head cape (natural head direction),
dimensions of the eye (cornea-pupil distance, pupil-lens distance, posterior chamber length, pupil size),
higher-order aberrations of the eye,
glare sensitivity.

The parameters related to the manner in which the given human wearer intends to use the real visual equipment may include activities. An activity is an action that involves vision, with or without a physical support, in a specific context and/or with a postural constraint. For instance, the activity may be watching a video, on a smartphone, while sitting on a couch.

Thus, the parameters related to the manner in which the given human wearer intends to use the real visual equipment may include various activities, such as precision manual work at close distance, using a smartphone, using a laptop, using a TV screen, cycling, etc.

The data related to the frame may include:

A, B, DBL sizes (where A is the eye size or lens size i.e. the horizontal dimension of a lens when mounted in the frame, B is the vertical dimension of a lens when mounted in the frame and DBL is the Distance Between Lenses or bridge size i.e. the horizontal distance between both lenses when mounted in the frame),
frame shape,
wearing parameters (pantoscopic tilt of the frame, wrap angle of the frame, vertex distance),
position of the center of rotation of the eyes,
fitting height.

The parameters regarding the lifestyle of the wearer relate to at least one type of activity in the course of which the given human wearer intends to use the real visual equipment. These parameters may be recorded in various ways. For example, the wearer may select several activities from a list, or he/she may attribute a rating to a list of activities, depending on their importance or on the wearer's preferences. Alternatively, lifestyle parameters can be obtained from real life data, for example with a connected device saving time spent on different activities.

The exact list of activities is not needed. On the other hand, the following parameters are advantageously obtained from a list of the considered human wearer's activities:

vision zones:
looking at a far distance;
looking at intermediate distance;
looking at near distance;
static/dynamic vision:
looking while in motion, or while the surroundings are moving;
transitioning between vision zones;
light environment:
indoor dim/bright;
outdoor dim/bright;
exposure to specific light environments.

The parameters regarding the environment describe in three dimensions the position of objects with respect to a world reference frame. The world reference frame is a 3D coordinate system (e.g. Cartesian or polar), the origin and orientation of which are arbitrary defined.

A virtual model of the environment may be defined in different ways:

via a software interface, with proper positioning and dimensions of models of key objects such as screens, windows, etc.; or
by starting from predefined objects (a desk, a car cockpit, a workshop) and by adjusting the dimensions and positions of the objects to match real objects in the considered human wearer's real environment;
the virtual model of the environment may be acquired by tridimensional scanning of real objects of the considered human wearer's real environment.

A virtual model of the wearer is also positioned in the world reference frame.

Another option is to describe the position of objects directly with respect to the wearer, for example using as an origin the cyclopean reference frame of the wearer. The cyclopean reference frame is a coordinate system (e.g. Cartesian or polar) centered at the cyclopean eye position. The cyclopean eye is a position, in the world reference frame, which represents a geometrical position between left and right eyes.

The device 10 also comprises a set of pre-selected ophthalmic lenses.

These ophthalmic lenses are pre-selected on the basis of the above-detailed plurality of parameters as possibly "good candidates" for the considered human wearer.

For example, the ECP, based on his/her knowledge and experience, can provide a pre-selection of lens designs or added values which may solve the wearer's ametropia or visual condition.

As another option, on a Web site or application, the customer can pre-select a number of designs based on price or other criteria. The Web site or application may also pre-filter the solutions automatically based on the wearer's physiological data, frame choice, etc.

As shown in FIG. 1, the device 10 also comprises at least one processor 14 that is configured, for each ophthalmic lens of the pre-selected set, to obtain a visual equipment model Me, a wearer model Mw and an environment and visual task model Mt and to evaluate a performance Perf of the visual equipment model Me worn by the wearer model Mw and combined with the environment and visual task model Mt, as detailed below.

The visual equipment model Me is a virtual model of a given one of the real visual equipments. It comprises at least one virtual ophthalmic lens that is defined by the same characteristics as the considered pre-selected ophthalmic lens of the set of pre-selected ophthalmic lenses.

In the present disclosure, the wearer model Mw is also referred to as an "avatar" of the human wearer. It is a virtual model of the human wearer. It is built from at least one parameter of the above-described plurality of parameters.

It may be built as described in document WO 2020/193436 A1, or it may consist of pre-recorded data obtained from a database, as proposed in document WO 2020/193370 A1.

In an embodiment, the at least one processor 14 is further configured to represent graphically the wearer model Mw carrying out a virtual model of the at least one real visual task in the environment and visual task model Mt.

In an embodiment, the wearer model Mw may comprise a movable head model. The head model is a virtual model of the human wearer's head.

In that embodiment, optionally, the head model may comprise at least one virtual eye, which is a virtual model of at least one eye of the human wearer. The virtual eye is rotationally movable with respect to the head model.

In such an embodiment, the above-described plurality of parameters may further comprise data related to motion of the human wearer's eye(s), in contribution to visual behavior, i.e. data related to eye motion that contribute to reflect the human wearer's visual behavior, and/or data related to motion of the human wearer's head, in contribution to visual behavior, i.e. data related to head motion that contribute to reflect the human wearer's visual behavior.

In embodiments where the wearer model Mw comprises a movable head model, optionally, the wearer model Mw may further comprise a virtual torso of the wearer, which is a virtual model of the human wearer's torso. The virtual torso may be movable in the environment and visual task model Mt. The head model may be rotationally movable with respect to the virtual torso.

In such an embodiment, the above-described plurality of parameters may further comprise data related to motion of the human wearer's torso, in contribution to visual behavior, i.e. data related to torso motion that contribute to reflect the human wearer's visual behavior.

The visual equipment model Me cooperates with the wearer model Mw.

The environment and visual task model Mt is a virtual model of the at least one real environment and the at least one real visual task mentioned above. It comprises at least a sequence of points to be looked at by the wearer model Mw.

The manner in which the above-described plurality of parameters other than the prescription Rx may be taken into account in the wearer model Mw is detailed below.

age: may be used to derive objective accommodation amplitude (for example according to the Duane model), ranges of motion of head and eyes, and kyphosis parameter;

gender: may be used to determine main body dimensions and kyphosis parameter;

half-pupillary-distances: may be used to position the eyes with respect to the head and to position the lenses in the frames;

height and main other dimensions of body: may be used to compute Harmon's distance and personalize some environment distances. By way of non-limiting example, the dimensions can be acquired by direct measurement or tridimensional scanning;

head and body axes and rotation centers: may be used to determine head and torso reference frames;

Harmon's distance, or reading distance: may be used as a reference for positioning near vision related objects;

maximum visual acuity: may be used to derive visual acuity in the presence of aberrations. Visual acuity is equal to maximum visual acuity minus acuity loss, where acuity loss may be determined according to a predetermined model such as the one described in document WO 2017/064065 A1 (another example of acuity calculation is described in document WO 2020/260481 A1);

visual acuity sensitivity to aberrations: may be used to modify the acuity loss model in case the wearer is more or less sensitive to wearer power or astigmatism errors;

objective/subjective accommodation reserve: may be used to compute acuity loss according to the above-mentioned acuity calculation model, where objective/subjective accommodation is used to determine power error when looking at a given object point;

range of motion of the head: may be used to personalize the head-eye coordination (e.g. limit positions of the range of motion, define an initial position corresponding to the minimal effort, define the variation of efforts between initial position and limit positions);

range of motion of the eyes: may also be used to personalize the head-eye coordination (e.g. limit positions of the range of motion, define an initial position corresponding to the minimal effort, define the variation of efforts between initial position and limit positions);

-kyphosis: may be used to define a reference postural angle of the head and torso;

-phorias: may be used to define a reference angle for gaze natural relaxed direction, which may in turn be used as a reference for gaze effort estimation;

fusional reserves: may be used to define a reference for individual ability to manage vergence amplitude in order to maintain binocular simple vision. It may in turn be used as a reference for binocular effort estimation;

sensory dominant eye: may be used to adjust the model of binocular acuity, as a blurry image on the sensory dominant eye is more disturbing than the same blur on the other eye;

head-eye coefficient: may be used to personalize the ratio of head-eye movements in head-eye coordination;

gaze dominant eye: may be used to modify the position of the cyclopean eye;

near vision behavior: may be used to define a reference position and angle for near vision object placement;

hand laterality: may be used to derive eye dominance, and to modify the position of objects in near vision;

head cape: may be used to determine posture efforts;

dimensions of the eye (cornea-pupil distance, pupil-lens distance, posterior chamber length, pupil size): may be used to personalize calculations based on eye geometry, for example aberrations or peripheral defocus;

higher-order aberrations of the eye: may be used for wavefront computations;

glare sensitivity: may be used to specify vision performance alteration in specific lighting conditions.

For obtaining the above-described plurality of parameters that will make it possible to individualize the "avatar", standard or existing equipment and measurements may be used, for example by the ECP. Optionally, at least some of the parameters may be obtained through a simple questionnaire to be answered by the wearer or customer, or through simple additional equipment, so that it is not necessary to conduct a detailed, time-consuming phase of individual parameter acquisition. Thus, no long time process in an ECP's store is needed.

By way of non-limiting example, as available standard equipment, the following may be cited: pupilometer for pupillary distance or half-pupillary distance, usual equipment for eye rotation center position and data related to the frame, phoropter for prescription Rx and acuity, phorias, etc.

A questionnaire will make it possible to obtain age, gender, height, activities, ethnicity, etc.

Non-limiting examples of simple additional equipment are:

a smart frame provided with an accelerometer and/or with an inclinometer and/or with an eye tracker, to derive some basic head/eye/torso measurements for a specific in-store activity such as reading or walking in the store, and to refine avatar parameters such as the "k" coefficient described in WO 2020/193436 A1;

a simple video camera, to record wearer body motion and replay it, as described in WO 2020/193370 A1.

At least some parameters of the above-described plurality of parameters may also be available on the cloud, or may be acquired at least partially from a computer and/or from smartphone via an embedded camera and then be used for online sales.

The manner in which the data related to the frame may be taken into account in the wearer model Mw is detailed below.

A, B, DBL sizes: may be used to derive the dimensions of the lenses;

frame shape: may be used to derive the contours of the lenses;

wearing parameters (pantoscopic tilt of the frame, wrap angle of the frame, vertex distance): may be used to derive the positioning of the lenses with respect to the eyes;

position of the center of rotation of the eyes: may be used to derive the positioning of the lenses with respect to the eyes, or the eyes with respect to the head;

fitting height: may be used to derive the positioning of the lenses in the frame.

Avatar simulations are described in detail in WO 2020/193436 A1. For example, for customizing the avatar, the gaze effort or the head posture effort may be considered and may differ depending on age, ethnicity or prescription.

Also the head rotation, defined by three angles denoted theta, phi and rho, may be calculated as a fraction of the elevation denoted theta_i and of the azimuth denoted phi_i of a fixation point, according to gain values (k_vertical, k_horizontal):

theta=k_vertical×theta_i
phi=k_horizontal×phi_i
rho=0

"k" coefficients may also be defined for different age, ethnicity, gender, prescription, etc.

The torso position can be customized via the considered human wearer's height.

The torso motion can be customized thanks to video recording of the considered human wearer.

The one or more parameters related to the given human wearer's lifestyle may also be used for modifying the above-mentioned environment and visual task model Mt, for more customization to the considered human wearer, which amounts to define customized scenarios based on lifestyle and environment input.

Simulations are run for each defined "scenario", with the visual equipment model Me corresponding to each pre-selected equipment. In the present disclosure, a scenario defines a combination of the wearer model Mw with the environment and visual task model Mt, i.e. it defines how a predetermined visual task comprising a sequence of fixation points is to be carried out by the wearer model Mw in an environment defined by a description of shapes and positions of elements to be viewed by the wearer model Mw.

The simulation output is a set of performance criteria for each combination of Mt and Me worn by the wearer model Mw.

Avatar performance criteria may include:

visual acuity, monocular or binocular, distortions, static or dynamic, postural efforts, postural flexibility, vergence efforts, accommodation efforts, binocular comfort, etc.

The performance Perf of each visual equipment model Me is evaluated by the at least one processor 14 based on the avatar performance criteria.

The one or more parameters related to the given human wearer's lifestyle may be used for weighting the above-mentioned performance Perf, which amounts to weighting the simulation results per scenario and combining them into overall performance criteria, thus taking into account, for example, the predominance of some activities for the considered human wearer.

The evaluation results may be used to demonstrate the benefit of the chosen design to the customer.

The consolidated simulation results may be presented to the wearer in order to help him/her decide which visual equipment is the best for him/her.

A graphical visualization of the avatar performing the scenarios may be presented to the wearer to help him understand the benefit of each equipment.

Several designs may remain as "best" equipment items, because of a trade-off in performance. In such a case, the simulation results may be used as a support for discussion e.g. between the ECP and the customer.

A non-limiting example of a visual equipment evaluation as provided according to the present disclosure by the device 10, or by the method, or by the computer program product, or by the non-transitory computer-readable storage medium, is detailed below.

Wearer Physiological Data:

Prescription:

right eye: 0 (0) 0° Add 2.50 left eye: 0 (0) 0° Add 2.50

Half-pupillary distances:

right eye: 32.5 mm left eye: 32.0 mm

Age: 62 years

Height: 172 cm

Gender: female

The wearer model Mw is as described in WO 2020/193436 A1. It comprises torso, head and eyes.

The prescriptions for the eyes are adjusted to the prescription of the human wearer.

The positions of the eyes are adjusted according to the human wearer's half-pupillary distances.

The kyphosis represented through the torso-head kinematics is adjusted according to the human wearer's age.

The objective accommodation of the eyes is adjusted according to the human wearer's age.

The position and sizes of torso and head are adjusted to the height of the human wearer.

Frame Data:

Size: A=56 mm, B=40 mm, rectangular frame shape, DBL=17.5 mm

Wearing conditions: pantoscopic tilt=8°, wrap angle=0°, vertex distance=12 mm

Fitting height=24 mm

The positions of the lenses in front of the eyes are adjusted according to the wearing parameters.

Lifestyle:

Precision manual work at close distance: no

Smartphone: yes, high usage, standard distance

Tablet: no

Laptop: yes, medium usage, standard distance

Desktop: no

TV screen: yes, low usage, distance=5 m

Driving: no

The ECP pre-selects 2 designs:

design A design B

The scenarios for the avatar are defined as follows:

Smartphone Task:

Object=smartphone

Size=70×140 mm

Position=40° down from cyclopean eye, distance from the center of rotation of the cyclopean eye=37 cm Fixation pattern=simulated reading pattern Maximum binocular acuity loss=0.05 log MAR Performance criterion: comfort area Laptop Task:

Object=laptop screen

Size=330×220 mm

Position=20° down from cyclopean eye, distance from the center of the cyclopean eye=60 cm Fixation pattern=simulated reading pattern Maximum binocular acuity loss=0.05 log MAR Performance criterion: comfort area TV Task:

Object=TV screen

Size=200×300 mm

Position=0° down from cyclopean eye, distance from the center of the cyclopean eye=500 cm Fixation pattern=simulated reading pattern Maximum binocular acuity loss=0.05 log MAR Performance Criterion: Comfort Area The simulation is directed to performance evaluation for the two items of visual equipment respectively based on the above-mentioned two pre-selected designs design A and design B. The average comfort area is evaluated for each task and each item of equipment.

Figure 2:
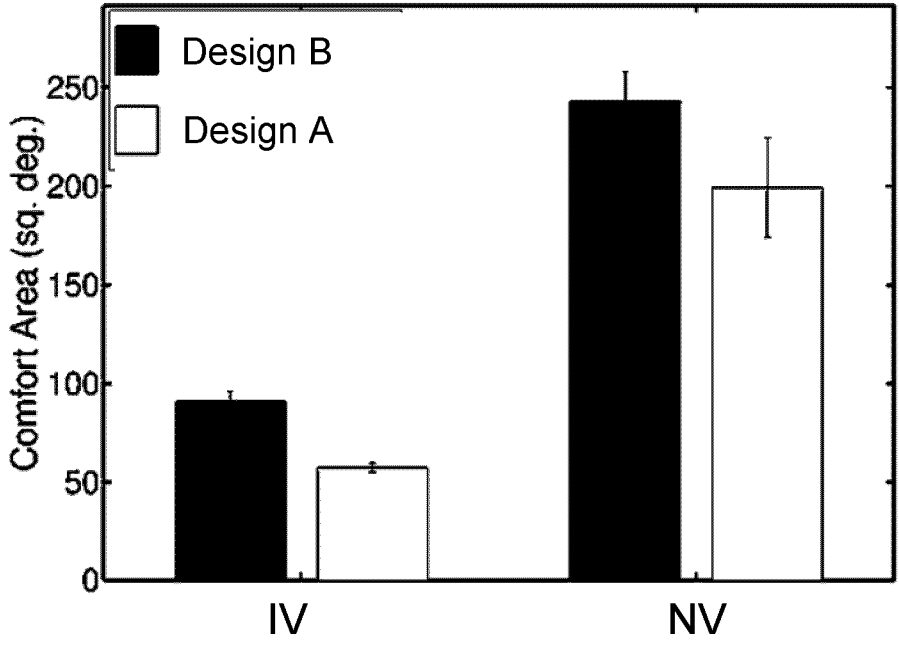
FIG. 2 is a graph illustrating a non-limiting example of results of performance evaluation according to the disclosure.

FIG. 2 summarizes the results of performance evaluation in the form of a graph, showing the comfort area, in square degrees, for each of the two visual equipment items, for the laptop task (on the left of the graph, where IV denotes intermediate vision) and for the smartphone task (on the right of the drawing, where NV denotes near vision).

As the performance on the TV screen is similar for both visual equipment items, it is not represented on the graph.

The graph shows that the visual equipment item based on the design B pre-selected design provides a better comfort area in IV and NV compared to the visual equipment item based on the design A pre-selected design. Thus, the ECP may use these results to recommend the visual equipment item based on design B.

Optionally, added values and lighting conditions may be taken into account to make recommendations about filters or anti-reflection coatings.

Thus, the device 10 may be used by an ECP to select or recommend to a specific wearer an optical design, a coating or a full visual equipment item.

Figure 3:
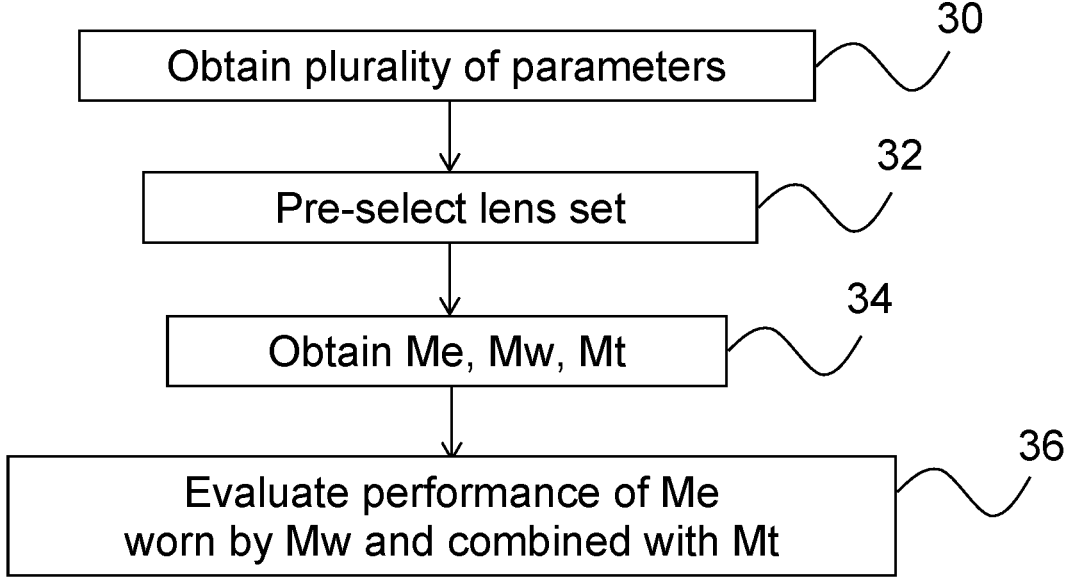
FIG. 3 is a flow diagram showing steps of a method according to the disclosure, in a particular embodiment.

The flow diagram of FIG. 3 shows steps of a method according to the disclosure for evaluating one or more visual equipment models respectively corresponding to one or more real visual equipments.

As described above in relationship with the device 10, the real visual equipments are for a human wearer to carry out at least one real visual task in at least one real environment. Each one of the real visual equipments comprises at least one ophthalmic lens.

As shown in FIG. 3, a first step 30 of the method comprises obtaining a plurality of parameters comprising at least a prescription Rx for at least one eye of the considered human wearer. The plurality of parameters may be for example as described above in relationship with the device 10.

A following step 32 comprises pre-selecting a set of ophthalmic lenses on the basis of the plurality of parameters obtained at step 30. The pre-selected lens set may be for example as described above in relationship with the device 10.

Following steps 34 and 36 are run by at least one processor, such as for example the processor 14, for each one of the ophthalmic lenses pre-selected at step 32.

Step 34 comprises obtaining a visual equipment model, which is a virtual model of a given one of the above-mentioned real visual equipments, the visual equipment model comprising at least one virtual ophthalmic lens defined by the same characteristics as the considered pre-selected ophthalmic lens. The obtained visual equipment model may be for example the visual equipment model Me described above in relationship with the device 10.

Step 34 also comprises obtaining a wearer model, which is a virtual model of the considered human wearer, the wearer model being built from at least one parameter of the plurality of parameters obtained at step 30 and the visual equipment model cooperating with the wearer model. The wearer model may be for example the wearer model Mw described above in relationship with the device 10.

Step 34 also comprises obtaining an environment and visual task model, which is a virtual model of the at least one real environment and of the at least one real visual task mentioned above. The environment and visual task model comprises a sequence of points to be looked at by the wearer model and is for example as described above in relationship with the device 10.

Then, step 36 comprises evaluating the performance of the visual equipment model worn by the wearer model and combined with the environment and visual task model, for example as described above in relationship with the device 10.

In a particular embodiment, the method according to the disclosure is computer-implemented. Namely, a computer program product comprises one or more sequences of instructions that are accessible to a processor and that, when executed by the processor, cause the processor to carry out steps of the method for evaluating a plurality of visual equipment models as described above.

The models Me, Mw and Mt may be built for example remotely in a cloud, or locally in a computer.

The sequence(s) of instructions may be stored in one or several non-transitory computer-readable storage medium/media, including a predetermined location in a cloud.

Although representative methods and devices have been described in detail herein, those skilled in the art will recognize that various substitutions and modifications may be made without departing from the scope of what is described and defined by the appended claims.

The invention claimed is:

1. A device for evaluating a plurality of visual equipment models respectively corresponding to a plurality of real visual equipment for a given human wearer of any one of said real visual equipment to carry out at least one real visual task in at least one real environment, each one of said real visual equipment comprising at least one ophthalmic lens, said device comprising:

at least one input configured to obtain a plurality of parameters comprising at least a prescription for at least one eye of said given human wearer;

a set of ophthalmic lenses pre-selected on the basis of said plurality of parameters, each pre-selected ophthalmic lens being defined by predetermined characteristics; and at least one processor configured, for each one of said pre-selected ophthalmic lenses, to:

obtain a visual equipment model, which is a virtual model of a given one of said real visual equipment, said visual equipment model comprising at least one virtual ophthalmic lens defined by the same characteristics as said one of said pre-selected ophthalmic lenses, obtain a wearer model, which is a virtual model of said given human wearer, said wearer model comprising a movable head model, which is a virtual model of a head of said given human wearer, said head model comprising at least one virtual eye, which is a virtual model of at least one eye of said given human wearer, said at least one virtual eye being rotationally movable with respect to said head model, said wearer model being built from at least one parameter of said plurality of parameters, said visual equipment model being worn by said wearer model, obtain an environment and visual task model, which is a virtual model of said at least one real environment and said at least one real visual task, said environment and visual task model comprising at least a sequence of points to be looked at by said wearer model, and evaluate a performance of said visual equipment model worn by said wearer model and combined with said environment and visual task model, according to a predetermined set of performance criteria including at least one of monocular or binocular visual acuity, static or dynamic distortions, postural efforts, postural flexibility, vergence efforts, accommodation efforts, or binocular comfort.

2. The device according to claim 1, wherein said plurality of parameters further comprises at least one parameter related to vision of said given human wearer.

3. The device according to claim 1, wherein said plurality of parameters further comprises at least one parameter related to a manner in which said given human wearer intends to use said any one of said real visual equipment.

4. The device according to claim 1, wherein said plurality of parameters further comprises at least one parameter related to said given human wearer's lifestyle, said lifestyle being related to at least one type of activity in a course of which said given human wearer intends to use said any one of said real visual equipment.

5. The device according to claim 4, wherein said at least one parameter related to said given human wearer's lifestyle is used for weighting said performance and/or for modifying said environment and visual task model.

6. The device according to claim 1, wherein said environment and visual task model comprises models of objects acquired by tridimensional scanning of real objects of said real environment.

7. The device according to claim 1, wherein said environment and visual task model comprises models of objects defined via a software interface.

8. The device according to claim 7, wherein said objects are taken among predefined objects, dimensions and/or positions of which are adjusted to match real objects of said real environment.

9. The device according to claim 1, wherein said plurality of parameters further comprises data related to motion of said at least one eye of said given human wearer, in contribution to visual behavior and/or to motion of said head of said given human wearer, in contribution to visual behavior.

10. The device according to claim 1, wherein:

said wearer model further comprises a virtual torso of said wearer, which is a virtual model of a torso of said given human wearer;

said virtual torso is movable in said environment and visual task model; and said head model is rotationally movable with respect to said virtual torso.

11. The device according to claim 10, wherein said plurality of parameters further comprises data related to motion of said torso of said given human wearer, in contribution to visual behavior.

12. The device according to claim 1, wherein said real visual equipment further comprises an eyeglasses frame and said plurality of parameters further comprises data related to said frame.

13. The device according to claim 1, wherein said at least one processor is further configured to represent graphically said wearer model carrying out a virtual model of said at least one real visual task in said environment and visual task model.

14. A computer-implemented method for evaluating a plurality of visual equipment models respectively corresponding to a plurality of real visual equipment for a given human wearer of any one of said real visual equipment to carry out at least one real visual task in at least one real environment, each one of said real visual equipment comprising at least one ophthalmic lens, said method comprising:

obtaining a plurality of parameters comprising at least a prescription for at least one eye of said given human wearer;

pre-selecting a set of ophthalmic lenses on the basis of said plurality of parameters, each pre-selected ophthalmic lens being defined by predetermined characteristics; and running the following by at least one processor for each one of said pre-selected ophthalmic lenses:

obtaining a visual equipment model, which is a virtual model of a given one of said real visual equipment, said visual equipment model comprising at least one virtual ophthalmic lens defined by the same characteristics as said one of said pre-selected ophthalmic lenses;

obtaining a wearer model, which is a virtual model of said given human wearer, said wearer model comprising a movable head model, which is a virtual model of a head of said given human wearer, said head model comprising at least one virtual eye, which is a virtual model of at least one eye of said given human wearer, said at least one virtual eye being rotationally movable with respect to said head model, said wearer model being built from at least one parameter of said plurality of parameters, said visual equipment model being word by said wearer model;

obtaining an environment and visual task model, which is a virtual model of said at least one real environment and said at least one real visual task, said environment and visual task model comprising at least a sequence of points to be looked at by said wearer model; and evaluating a performance of said visual equipment model worn by said wearer model and combined with said environment and visual task model, according to a predetermined set of performance criteria including at least one of monocular or binocular visual acuity, static or dynamic distortions, postural efforts, postural flexibility, vergence efforts, accommodation efforts, or binocular comfort.

15. A non-transitory computer-readable storage medium including computer executable instructions, wherein the instructions, when executed by a processor, cause the processor to perform a method for evaluating a plurality of visual equipment models respectively corresponding to a plurality of real visual equipment for a given human wearer of any one of said real visual equipment to carry out at least one real visual task in at least one real environment, each one of said real visual equipment comprising at least one ophthalmic lens, the method comprising:

obtaining a plurality of parameters comprising at least a prescription for at least one eye of said given human wearer;

pre-selecting a set of ophthalmic lenses on the basis of said plurality of parameters, each pre-selected ophthalmic lens being defined by predetermined characteristics; and running the following for each one of said pre-selected ophthalmic lenses:

obtaining a visual equipment model, which is a virtual model of a given one of said real visual equipment, said visual equipment model comprising at least one virtual ophthalmic lens defined by the same characteristics as said one of said pre-selected ophthalmic lenses;

obtaining a wearer model, which is a virtual model of said given human wearer, said wearer model comprising a movable head model, which is a virtual model of a head of said given human wearer, said head model comprising at least one virtual eye, which is a virtual model of at least one eye of said given human wearer, said at least one virtual eye being rotationally movable with respect to said head model, said wearer model being built from at least one parameter of said plurality of parameters, said visual equipment model being worn by said wearer model;

obtaining an environment and visual task model, which is a virtual model of said at least one real environment and said at least one real visual task, said environment and visual task model comprising at least a sequence of points to be looked at by said wearer model; and evaluating a performance of said visual equipment model worn by said wearer model and combined with said environment and visual task model, according to a predetermined set of performance criteria including at least one of monocular or binocular visual acuity, static or dynamic distortions, postural efforts, postural flexibility, vergence efforts, accommodation efforts, or binocular comfort.

\* \* \* \* \*